United States Patent [19]

Sharma et al.

[11] Patent Number: 5,229,130
[45] Date of Patent: Jul. 20, 1993

[54] VEGETABLE OIL-BASED SKIN PERMEATION ENHANCER COMPOSITIONS, AND ASSOCIATED METHODS AND SYSTEMS

[75] Inventors: Kuldeepak Sharma, Mountain View; Eric J. Roos, Menlo Park; Darth M. Dunbar, San Mateo, all of Calif.

[73] Assignee: Cygnus Therapeutics Systems, Redwood City, Calif.

[21] Appl. No.: 810,963

[22] Filed: Dec. 20, 1991

[51] Int. Cl.$^5$ .............................................. A61F 13/00
[52] U.S. Cl. .................................. 424/449; 424/448; 514/946; 514/947
[58] Field of Search ............... 424/449, 448; 514/946, 514/947

[56] References Cited

U.S. PATENT DOCUMENTS

| | | | |
|---|---|---|---|
| 3,472,931 | 10/1969 | Stoughton | 424/180 |
| 3,551,554 | 12/1970 | Herschler | 424/7 |
| 3,989,816 | 11/1976 | Rajadhyaksha | 424/60 |
| 4,066,218 | 2/1977 | Sipos | 424/54 |
| 4,316,893 | 2/1982 | Rajadhyaksha | 424/180 |
| 4,379,454 | 4/1983 | Campbell et al. | 604/897 |
| 4,405,616 | 9/1983 | Rajadhyaksha | 424/244 |
| 4,440,777 | 4/1984 | Zupan | 424/274 |
| 4,537,776 | 8/1986 | Cooper | 514/424 |
| 4,552,872 | 11/1985 | Cooper et al. | 514/175 |
| 4,557,934 | 12/1985 | Cooper | 424/128 |
| 4,568,343 | 2/1986 | Leeper et al. | 604/896 |
| 4,626,539 | 12/1986 | Aungst | 514/282 |
| 4,746,515 | 5/1988 | Cheng et al. | 424/449 |
| 4,764,379 | 8/1988 | Sanders et al. | 424/449 |
| 4,783,450 | 11/1988 | Fawzi et al. | 514/78 |
| 4,900,555 | 2/1990 | Cheng | 424/447 |
| 4,904,699 | 2/1990 | Bauer | 514/972 |
| 4,913,905 | 4/1990 | Fankhauser | 424/449 |
| 5,019,395 | 5/1991 | Mahjour | 424/449 |

FOREIGN PATENT DOCUMENTS

| | | |
|---|---|---|
| 043738 | 1/1982 | European Pat. Off. . |
| 0261429 | 3/1988 | European Pat. Off. . |
| 0272987 | 6/1988 | European Pat. Off. . |

Primary Examiner—Thurman K. Page
Assistant Examiner—D. Gabrielle Phelan
Attorney, Agent, or Firm—Morrison & Foerster

[57] ABSTRACT

Methods and compositions are provided which increase the permeability of skin to transdermally administered pharmacologically active agents. The compositions are formulated with one or more vegetable oils as skin permeation enhancers; a preferred composition contains both coconut oil and soybean oil. Drug delivery systems for administering drugs transdermally in combination with the vegetable oil-based enhancer compositions are provided as well.

48 Claims, No Drawings

VEGETABLE OIL-BASED SKIN PERMEATION ENHANCER COMPOSITIONS, AND ASSOCIATED METHODS AND SYSTEMS

TECHNICAL FIELD

This invention relates generally to methods and compositions for enhancing the permeability of the skin to pharmacologically active agents, and more particularly to novel skin permeation enhancer compositions containing vegetable oil mixtures.

BACKGROUND

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences—e.g., gastrointestinal irritation and the like—are eliminated as well. Transdermal drug delivery also makes possible a high degree of control over blood concentrations of any particular drug.

Skin is a structurally complex, relatively thick membrane. Molecules moving from the environment into and through intact skin must first penetrate the stratum corneum and any material on its surface. They must then penetrate the viable epidermis, the papillary dermis, and the capillary walls into the blood stream or lymph channels. To be so absorbed, molecules must overcome a different resistance to penetration in each type of tissue. Transport across the skin membrane is thus a complex phenomenon. However, it is the cells of the stratum corneum which present the primary barrier to absorption of topical compositions or transdermally administered drugs. The stratum corneum is a thin layer of dense, highly keratinized cells approximately 10-15 microns thick over most of the body. It is believed to be the high degree of keratinization within these cells as well as their dense packing which creates in most cases a substantially impermeable barrier to drug penetration.

In order to increase skin permeability, and in particular to increase the permeability of the stratum corneum (i.e., so as to achieve enhanced penetration, through the skin, of the drug to be administered transdermally), the skin may be pretreated with a penetration enhancing agent (or "permeation enhancer", as sometimes referred to herein) prior to application of a drug. Alternatively, and preferably, a drug and a permeation enhancer are concurrently delivered.

The present invention is directed to a novel method and composition for enhancing the penetration of a drug through skin. The invention is premised on the discovery that certain vegetable oils used individually or in combination are effective in enhancing the penetration of pharmacologically active agents through the skin.

While there are a number of patents and publications which relate to the use of a variety of different skin permeation enhancers, applicants are unaware of any art which relates to the use of vegetable oils as disclosed herein as skin permeation enhancers.

The following references relate generally to the use of permeation enhancers in transdermal formulations. U.S. Pat. Nos. 4,006,218, 3,551,554 and 3,472,931, for example, respectively describe the use of dimethylsulfoxide (DMSO), dimethyl formamide (DMF) and N,N-dimethylacetamide (DMA) to enhance the absorption of pharmacologically active agents through the stratum corneum. Other compounds which have been used to enhance skin permeability include: decylmethylsulfoxide ($C_{10}MSO$); Transcutol, cited in the preceding section; polyethylene glycol monolaurate (PEGML); (see, e.g., U.S. Pat. No. 4,568,343); glycerol monolaurate (U.S. Pat. No. 4,746,515); propylene glycol monolaurate (see European Patent Application No. 87402945.7, Published as EP Publication No. 272 987, which derives from U.S. patent application Ser. No. 945,356, filed 22 Dec. 1986, of common assignment herewith); ethanol (e.g., as in U.S. Pat. No. 4,379,454); eucalyptol (U.S. Pat. No. 4,440,777); lecithin (U.S. Pat. No. 4,783,450); the 1-substituted azacycloheptan-2-ones, particularly 1-n-dodecylcyclazacycloheptan-2-one (available under the trademark Azone ® from Nelson Research & Development Co., Irvine, Calif.; see U.S. Pat. Nos. 3,989,816, 4,316,893, 4,405,616 and 4,557,934); propylene glycol in combination with a fatty acid such as linoleic acid (European Patent Publication No. 261429); "cell envelope disordering compounds" such as methyl laurate or oleic acid in combination with N-(hydroxyethyl) pyrrolidone (U.S. Pat. No. 4,537,776) or $C_3$–$C_4$ diols (U.S. Pat. No. 4,552,872, European Patent Application Publication No. 043738). U.S. Pat. No. 4,764,379 discloses a binary enhancer composition of ethanol and glycerol monolaurate.

DISCLOSURE OF THE INVENTION

Accordingly, it is an object of the present invention to provide a method for enhancing the flux of the drug through the skin comprising transdermally administering the drug in combination with a permeation-enhancing amount of a vegetable oil as will be described herein.

It is another object of the present invention to provide such a method in which the vegetable oil composition is a mixture of vegetable oils.

It is still another object of the invention to provide a composition of matter for delivering a drug through the skin which comprises: (a) a therapeutically effective amount of at least one drug; and (b) a permeation-enhancing amount of a vegetable oil composition as will be described in detail herein.

It is a further object of the invention to provide transdermal delivery systems for using the aforementioned compositions and carrying out the administration method.

Additional objects, advantages and novel features of the invention will be set forth in part in the description which follows, and in part will become apparent to those skilled in the art upon examination of the following, or may be learned by practice of the invention.

In one aspect of the invention, a method is provided for enhancing the flux of the drug through the skin, comprising transdermally administering the drug in combination with a permeation-enhancing amount of a vegetable oil composition containing at least one vegetable oil selected from the group consisting of almond oil, babassu oil, castor oil, Clark A oil, coconut oil, corn oil, cotton seed oil, jojoba oil, linseed oil, mustard oil, olive oil, palm oil, peanut oil, safflower oil, sesame oil, soybean oil, sunflower-seed oil and wheat germ oil. Preferred vegetable oils are those which do not contain large amounts of saturated fatty acids or large amounts of fatty acids containing less than about eight or more than about fourteen carbon atoms. Accordingly, preferred vegetable oils within the aforementioned group include coconut oil, corn oil, cotton seed oil, linseed oil, mustard oil, olive oil, palm oil, peanut oil, safflower oil and soybean oil. With most drugs, mixtures of vegetable oils appear to be preferred rather than individual vegetable oils, and a particularly preferred vegetable oil composition for use herein is a mixture of coconut oil and soybean oil.

In another aspect of the invention, a composition of matter is provided that is useful for the delivery of a drug through the skin, which comprises a therapeutically effective amount of the drug to be administered and a permeation-enhancing amount of a vegetable oil composition which contains at least one vegetable oil selected from the aforementioned group.

In still another aspect of the invention, a transdermal system is provided which is useful for the administration of a drug through the skin, wherein the system includes a source of the drug to be administered, a source of a permeation enhancer composition effective to increase the flux of the drug through the skin, wherein the permeation enhancer composition contains at least one vegetable oil, and wherein the system further includes a means for maintaining the system in drug and enhancer composition transmitting relationship to the skin, e.g., a contact adhesive layer which serves as the basal surface of the system and adheres to the skin during use.

MODES FOR CARRYING OUT THE INVENTION

Before describing the present invention in detail, it is to be understood that this invention is not limited to particular drugs or transdermal systems described herein as such may, of course, vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the content clearly dictates otherwise. Thus, for example, reference to "a vegetable oil" includes a mixture of two or more vegetable oils, reference to "a drug" includes reference to one or more drugs, and the like.

In describing and claiming the present invention, the following terminology will be used in accordance with the definitions set out below "Penetration enhancement" or "permeation enhancement" as used herein relates to an increase in the permeability of skin to a pharmacologically active agent, i.e., so as to increase the rate at which the drug permeates through the skin and enters the bloodstream. The enhanced permeation effected through the use of such enhancers, and, in particular, through the use of the enhancer composition of the present invention, can be observed by measuring the rate of diffusion of drug through animal or human skin using a diffusion cell apparatus as described in the Examples herein By "transdermal" delivery, applicants intend to include both transdermal (or "percutaneous") and transmucosal administration, i.e., delivery by passage of a drug through the skin or mucosal tissue and into the bloodstream.

"Carriers" or "vehicles" as used herein refer to carrier materials suitable for transdermal drug administration, and include any such materials known in the art, e.g., any liquid, gel, solvent, liquid diluent, solubilizer, or the like, which is nontoxic and which does not interact with other components of the composition in a deleterious manner. Examples of suitable carriers for use herein include water, silicone, liquid sugars, waxes, petroleum jelly, and a variety of other materials.

By the term "pharmacologically active agent" or "drug" as used herein is meant any chemical material or compound suitable for transdermal or trans mucosal administration which induces a desired systemic effect. Such substances include the broad classes of compounds normally delivered through body surfaces and membranes, including skin. In general, this includes: antiinfectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmic; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers.

Preferred drugs for use in conjunction with the enhancer composition of the present invention include narcotic analgesics such as buprenorphine or salts thereof (e.g., buprenorphine hydrochloride), antianxiety drugs such as alprazolam, hyponetic/sedative drugs such as triazolam, calcium channel blockers or antianginal drugs such as nifedipine, and antineoplastics such as tamoxifen.

By "therapeutically effective" amount of a pharmacologically active agent is meant a nontoxic but sufficient amount of a compound to provide the desired therapeutic effect. An "effective" amount of a permeation enhancer as used herein means an amount that will provide the desired increase in skin permeability and, correspondingly, the desired depth of penetration, rate of administration, and amount of drug delivered.

In a preferred embodiment, as noted above, the enhancer composition of the invention is a vegetable oil composition which contains at least one vegetable oil as described above. In a particularly preferred embodiment, the vegetable oil composition is a mixture of coconut oil and soybean oil; such compositions will include on the order of 10 wt. % percent to 90 wt. % coconut oil, and, correspondingly, 90 wt. % to 10 wt. % soybean oil. An exemplary coconut oil/soybean oil mixture is that manufactured and sold under the trademark Drewmulse ® D-4661, available from Stepan, Marywood, N.J. The combination of coconut and soybean oil has been found by the inventors herein to be far superior to most other permeation enhancers which are currently commercially available and is, furthermore, superior to the use of particular vegetable oils used individually, at least with some drugs.

The composition may in addition include one or more selected carriers or excipients, and various agents and ingredients commonly employed in dermatological ointments and lotions. For examples, fragrances, opacifiers, preservatives, anti-oxidants, gelling agents, perfumes, thickening agents, stabilizers, surfactants, emollients, coloring agents, and the like may be present. The composition may also include additional permeation enhancers, e.g., dimethylsulfoxide (DMSO), dimethyl formamide (DMF), N,N-dimethylacetamide (DMA), decylmethylsulfoxide ($C_{10}MSO$), polyethylene glycol monolaurate (PEGML), glycerol monolaurate, lecithin, the 1-substituted azacycloheptan-2-ones, particularly 1-n-dodecylcyclazacycloheptan-2-one (available under the trademark Azone® from Nelson Research & Development Co., Irvine, Calif.), alcohols, and the like. Particularly preferred additional enhancers for use in conjunction with the present invention are those described in commonly assigned U.S. Pat. No. 5,059,426 to Chiang et al., i.e., containing an ether component selected from the group consisting of diethylene glycol monoethylether, diethylene glycol monomethylether, and mixtures thereof, and an ester component given by the formula $[CH_3(CH_2)_mCOO]_nR$ in which m is an integer in the range of 8 to 16, n is 1 or 2, and R is a lower alkyl ($C_1$–$C_3$) residue that is either unsubstituted or substituted with one or two hydroxyl groups. The disclosure of the aforementioned patent is hereby incorporated by reference in its entirety.

The relative amounts of the components in these compositions can vary a great deal. For example, the amount of drug or drugs present in the composition will depend on a variety of factors, including the disease to be treated, the nature and activity of the drug, the desired effect, possible adverse reactions, the ability and speed of the drug to reach its intended target, and other factors within the particular knowledge of the patient and physician. The amount of enhancer present in the composition will similarly depend on a number of factors, e.g., on the depth of cutaneous penetration desired, the strength of the particular enhancer, the specific drug or drugs selected, and the like. Preferred compositions will typically contain on the order of about 1 wt. % to 10 wt. % drug, and about 5 wt. % to 25 wt. % enhancer, with the remainder of the composition being either a liquid or polymeric carrier (including optional additives as outlined above). The enhancer portion of the composition may contain only vegetable oil or it may contain vegetable oil in combination with additional skin permeation enhancers as described above. It is preferred, however, that the compositions of the present invention contain on the order of from about 5 wt. % to 10 wt. % vegetable oil.

The method of delivery of the present compositions may also vary, but necessarily involves application of the selected composition to a defined surface of the skin or other tissue for a period of time sufficient to provide the desired blood level of drug for the desired period of time. The method may involve direct application of the composition as an ointment, gel, cream, or the like, or may involve use of a drug delivery device as taught, for example, in U.S. Pat. Nos. 3,742,951, 3,797,494 and 4,568,343. The method may also involve pre-treatment of the skin with a vegetable oil enhancer to increase the permeability of the skin to the applied drug.

A transdermal delivery system can be constructed with the enhancer composition described hereinabove to deliver drugs for sustained drug delivery. The targeted skin flux for delivery of a particular drug can be achieved by adjusting vehicle composition and vehicle loading, as well as by adjusting the surface area through which the compositions are administered to skin.

Preferred transdermal drug delivery systems for use herein contain one or more drug/permeation enhancer reservoirs, a backing layer, and optionally one or more additional layers as those skilled in the art of transdermal drug delivery will readily appreciate.

The drug/permeation enhancer reservoir(s) will typically be in the form of a matrix comprising rubber or other polymeric material, e.g., natural and synthetic rubbers such as polybutylene, polyisobutylene, polybutadiene, polyethylene, styrene-butadiene copolymers, polyisoprene, polyurethane, copolyesters, ethylene/acrylic copolymers, polyether amides, silicones and their copolymers, and butadiene/acrylonitrile copolymers, ethylene vinyl acetate, gelled or thickened mineral oil, petroleum jelly and various aqueous gels and hydrophilic polymers that may serve as thickening agents. The matrix is applied to skin using a suitable adhesive as described, for example, in U.S. Pat. No. 4,568,343, supra. In some cases, the matrix may itself be comprised of an adhesive material.

The drug reservoir layer is formulated so as to contain the selected pharmacologically active agent(s) as well as the above enhancer composition. In a preferred embodiment, the layer will contain about 1 wt. % to 10 wt. % drug, 5 wt. % to 25 wt. % total enhancer and 65 wt. % to 94 wt. % polymeric adhesive and optionally tackifiers, surfactants or other additives. The pressure-sensitive adhesive which serves as the reservoir for this mixture is typically a polyisobutylene, silicone or acrylate adhesive. The layer may be formulated so that the selected drug is contained therein below saturation, at saturation, or in excess.

The backing membrane, which may be either occlusive or nonocclusive, is preferably comprised of a flexible, stretchable, polymer film, e.g., of polyether urethane, polyester urethane, polyamide, or other related copolymers. The material and thickness selected for the backing membrane is preferably such that a transdermal system can be provided having good wearability for at least a seven-day application.

The vegetable oil skin permeation enhancer compositions of the present invention give rise to a number of advantages which are unsuggested by the prior art of which applicants are aware. First, the particularly preferred mixture of soybean oil and coconut oil provides for a very high skin flux relative to other types of enhancers (as may be deduced in the examples below). In addition, it has been found that vegetable oils in general produce virtually no skin irritation or sensitization problems. Indeed, the inclusion of vegetable oils in transdermal formulations appears to reduce the skin irritation and sensitization which is problematic with some drugs. Finally, the vegetable oil compositions that are the focus of the present invention have been found to be completely compatible with a wide variety of drugs in transdermal formulations.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains

EXPERIMENTAL

In vitro Franz flow-through cells were used to compare the penetration of various drug-enhancer formulations through skin. A piece of human cadaver skin was mounted between the two half-cells and fastened with a clamp.

Drug-enhancer solutions (prepared with different drugs and enhancers as will be described individually for each example herein) were applied to the donor compartment to start the experiment. The receiver compartment was filled with distilled, deionized water and the temperature was maintained at 32° C. Samples were taken at preset time intervals and assayed by HPLC. The flux was calculated from the slope of the cumulative amounts of drug in the receiver compartment versus time.

EXAMPLE 1

The above procedure was used to evaluate the penetration of buprenorphine hydrochloride through skin using a variety of vehicles. In Table 1, results obtained with mixtures of coconut oil, soybean oil, almond oil, and olive oil with mineral oil are set forth. All oils were obtained from Stepan, Marywood, N.J., except for babassu oil (Croda, N.Y.) and Clark A oil (obtained from the J S & A Group, Northbrook, Ill.). In Table 2, penetration of buprenorphine hydrochloride through skin is evaluated in coconut oil, soybean oil, almond oil, olive oil, and mixed vegetable oil (Drewmulse ® D-4661; see above) versus buprenorphine in mineral oil as a control. Tables 3 and 4 represent still further flux studies with buprenorphine hydrochloride. In those tables, "PG" represents propylene glycol. As may be deduced from the tables, the mixed vegetable oil seemed to be the most effective in enhancing total buprenorphine skin flux.

The abbreviations used in the tables are as follows: "Bu HCl" represents buprenorphine hydrochloride, "Q" represents total cumulative amount of drug permeated, "TEWL" represents transepidermal water loss, "F" and "M" represent female and male, "PG" represents propylene glycol, "PEG" represents polyethylene glycol, and "mixed vegetable oil" represents the Drewmulse ® D-4661 mixture of coconut oil and soybean oil.

TABLE 1

Skin Flux Values for Various Liquid Donor Formulations

| Formulation | Q ± sd (μg/cm$^2$) | Enhancement Factor | Flux ± sd (mcg/cm$^2$/hr) | Enhancement Factor |
|---|---|---|---|---|
| 5% Bu HCl in mineral oil (control) | 1.76 ± 0.6 | 1 | 0.04 ± 0.0 | 1 |
| 5% Bu HCl in 10% coconut oil & 85% mineral oil | 3.60 ± 0.62 | 2 | 0.09 ± 1.53 | 2 |
| 5% Bu HCl in 10% soybean oil & 85% mineral oil | 4.10 ± 3.12 | 2 | 0.10 ± 0.08 | 2 |
| 5% Bu HCl in 10% almond oil & 85% mineral oil | 2.69 ± 0.33 | 1.5 | 0.06 ± 0.02 | 1.5 |
| 5% Bu HCl in 10% olive oil & 85% mineral oil | 2.96 ± 0.43 | 1.7 | 0.07 ± 0.01 | 1.8 |

TABLE 2

Skin Flux Values for Various Liquid Donor Formulations

| Formulation | Q ± sd (μg/cm$^2$) | Enhancement Factor | Flux ± sd (mcg/cm$^2$/hr) | Enhancement Factor |
|---|---|---|---|---|
| 5% Bu HCl in mineral oil (control) | 1.76 ± 0.6 | 1 | 0.04 ± 0.0 | 1 |
| 5% Bu HCl in 10% mixed vegetable oil and 85% mineral oil | 17.95 ± 1.42 | 10 | 0.41 ± 0.03 | 10 |
| 5% Bu HCl in 10% coconut oil and 85% mineral oil | 1.89 ± 0.49 | 1 | 0.05 ± 0.01 | 1.3 |
| 5% Bu HCl in 10% soybean oil and 85% mineral oil | 1.04 ± 0.44 | 1 | 0.02 ± 0.01 | 0.5 |
| 5% Bu HCl in 10% almond oil and 85% mineral oil | 1.24 ± 0.58 | 0.7 | 0.03 ± 0.01 | 0.8 |
| 5% Bu HCl in 10% olive oil and 85% mineral oil | 0.72 ± 0.35 | 0 | 0.02 ± 0.01 | 0.5 |

TABLE 3

Buprenorphine HCl Skin Flux from Various Formulations Through Different Batches of Skin

| Study # | 1 | 2 | 3 |
|---|---|---|---|
| Skin Batch | 90-31, 37 yrs, F, Thigh | 90-42, 98 yrs, F, Leg | 90-32, 37 yrs, F, Breast |
| TEWL | 12.60 ± 0.91 | 14.54 ± 1.28 | 5.17 ± 0.65 |
| #) Formulation | Flux (μg/cm$^2$/hr) | Flux (μg/cm$^2$/hr) | Flux (μg/cm$^2$/hr) |
| 1) 2.8% Bu HCl in PG | 0.36 ± 0.09 | 0.19 ± 0.08 | 0.09 ± 0.02 |
| 2) 2.8% Bu HCl + 2.8% Mixed Vegetable oils in PG | 8.79 ± 1.9 | 7.25 ± 7.1 | 10.4 ± 8.6 |

TABLE 4

Skin Flux Values for Various Liquid Donor Formulations

| Formulation* | Flux ± sd (mcg/cm²/hr) | Enhancement Factor | Q ± sd (μg/cm²) |
|---|---|---|---|
| 2.8% mixed vegetable oils | 7.25 ± 7.1 | 38 | 224.4 ± 224.6 |
| 2.8% Cocamidopropyl Betaine | 0.074 ± 0.04 | 0.4 | 4.84 ± 0.62 |
| 2.8% Disodium Laureth Sulfosuccinate | 0.366 ± 0.18 | 2 | 15.63 ± 7.2 |
| 2.8% HCl in PG | 0.189 (0.266, 0.113) | 1 | 4.5 (2.0, 7.0) |

*All formulations were liquid donors and included 2.8% Bu HCl in PG.

EXAMPLE 2

The same procedure was used to evaluate the penetration of alprazolam through skin, again using a variety of skin permeation enhancer formulations. Results are summarized in Tables 5 and 6 (abbreviations used are as in Example 1).

TABLE 5

Alprazolam Skin Flux

| # Formulation | Flux (μg/cm²/hr) | Cumulative amount of Alprazolam after 48 hr (μg/cm²) |
|---|---|---|
| 1) Alprazolam saturated in PG | 0.12<br>0.18<br>0.16<br>Av. = 0.15 ± 0.03 | 4.61<br>7.42<br>6.34<br>Av. = 6.12 ± 1.42 |
| 2) Alprazolam (saturated) + 10% Olive Oil in PG | 0.65<br>0.54<br>0.64<br>Av. = 0.61 ± 0.05 | 13.72<br>5.91<br>16.39<br>Av. = 12.01 ± 5.45 |
| 3) Alprazolam (saturated) + 10% Coconut Oil in PG | 0.33<br>0.35<br>0.15<br>Av. = 0.28 ± 0.11 | 28.81<br>22.39<br>25.46<br>Av. = 25.55 ± 3.20 |
| 4) Alprazolam (saturated) + 10% Almond Oil in PG | 0.18<br>0.18<br>0.36<br>Av. = 0.24 ± 0.10 | 6.99<br>7.93<br>14.27<br>Av. = 9.73 ± 3.96 |
| 5) Alprazolam (saturated) + 10% Mixed Vegetable Oil-PG | 15.11<br>49.99<br>17.64<br>Av. = 27.55 ± 19.49 | 602.4<br>1652.9<br>718.1<br>Av. = 991.1 ± 576 |

TABLE 6

Alprazolam Skin Flux from Various Formulations Through Different Batches of Skin

| Study # | 1 | 2 | 3 |
|---|---|---|---|
| Skin Batch | 90-42, 98 yrs, F, Leg | 90-45, 88 yrs, F, Thigh | 90-30, 62 yrs, F, Breast |
| TEWL | 14, 54 | 31.1 | 6.36 |
| #) Formulation | Flux (μg/cm²/hr) | Flux (μg/cm²/hr) | Flux (μg/cm²/hr) |
| 1) Alprazolam (saturated) in PG | 0.19 (0.22, 0.16) | 0.34 ± 0.07 | 0.16 ± 0.01 |
| 2) Alprazolam (saturated) + 10% PGML in PG | 15.83 ± 5.93 | | 13.96 (13.92, 14.00) |
| 3) Alprazolam (saturated) + 10% Mixed Vegetable Oil in PG | | 5.09 ± 0.02 | 175.50 ± 38.55 |

Again, the use of the mixed vegetable oil was found to provide significant enhancement relative to other enhancer formulations.

EXAMPLE 3

The above method was then used to compare the penetration of triazolam through the skin using a number of different skin permeation enhancer formulations. Tables 7 and 8 summarize the results (abbreviations used are as in Example 1).

TABLE 7

Triazolam Skin Flux

| # Formulation | Flux (μg/cm²/hr) | Cumulative Amount of Triazolam After 48 hr (μg/cm²) |
|---|---|---|
| 1) Triazolam saturated in PG | 0.062<br>0.041<br>0.042<br>Av. = 0.0051 ± 0.01 | 4.01<br>1.65<br>1.64<br>Av. = 2.43 |
| 2) Triazolam (saturated) + 10% Olive Oil in PG | 0.064<br>0.052<br>0.044<br>Av. = 0.053 ± 0.01 | 2.55<br>3.11<br>2.51<br>Av. = 2.72 ± 0.33 |
| 3) Triazolam (saturated) + 10% Coconut Oil in PG | 0.213<br>0.099<br>0.174<br>Av. = 0.161 ± 0.06 | 9.41<br>3.89<br>6.92<br>Av. = 6.76 ± 2.73 |
| 4) Triazolam (saturated) + 10% Almond Oil in PG | 0.065<br>0.088<br>0.514<br>Av. = 0.222 | 9.01<br>11.62<br>21.48<br>Av. = 14.04 |
| 5) Triazolam (saturated) + 10% Mixed Vegetable Oil-PG | 6.359<br>4.879<br>3.462<br>Av. = 4.91 ± 1.45 | 252.19<br>195.54<br>137.41<br>Av. = 195.04 ± 57.39 |

TABLE 8

Triazolam Skin Flux

| # Formulation | Flux (μg/cm²/hr) | Cumulative amount of Triazolam After 48 hr (μg/cm²/hr) |
|---|---|---|
| 1) Triazolam saturated in PG | 0.127<br>0.077<br>0.069<br>Av. = 0.091 ± 0.031 | 6.263<br>3.215<br>2.765<br>Av. = 4.081 ± 1.90 |
| 2) Triazolam (saturated) + 10% PGML in PG | 16.11<br>8.744<br>1.074<br>Av. = 8.642 ± 7.52 | 658.8<br>377.4<br>44.99<br>Av. = 360.4 ± 307.3 |
| 3) Triazolam (saturated) + 10% Glyceryl Monooleate in PG | 1.238<br>1.76<br>0.51<br>Av. = 1.166 ± 0.63 | 51.95<br>74.14<br>20.44<br>Av. = 48.84 ± 26.9 |
| 4) Triazolam (saturated) + 10% Mixed Vegetable Oil in PG | 1.77<br>6.12<br>12.24<br>Av. = 6.71 ± 5.25 | 75.46<br>265.1<br>524.7<br>Av. = 288.42 ± 225.5 |

Again, as with the preceding examples, the use of mixed vegetable oils as a skin permeation enhancer composition provided a very significant increase in skin flux relative to the other enhancer formulations tested.

EXAMPLE 4

The above method was used to compare the penetration of nifedipine through the skin using a variety of permeation enhancer formulations. Results are summarized in Table 9. In the table, "NFD" represents nifedipine. Babassu oil is a mixture of lauric/myristic/palmitic/stearic/oleic/linoleic fatty acids. Clark A oil consists of oxygenated peanut oil, peach kernel oil, grape seed oil, botanical complex XXI, essential oils (45% borneol, rosemary, terenbenthine, eucalyptus, arnica, juniper (trace element complex), 100% pure plant extract).

TABLE 9

Nifedipine Average Cumulative Release and Skin Flux Values for Various Oils Used in Feasibility Study

| Formulation | Q ± sd (μg/cm²) | Flux ± sd (mcg/cm²/hr) |
| --- | --- | --- |
| 1. NFD saturated in mixed vegetable oil | 0.77 ± 0.07 | 33.32 ± 2.74 |
| 2. NFD saturated in olive oil | 0.13 ± 0.01 | 6.03 ± 0.33 |
| 3. NFD saturated in almond oil | 0.11 ± 0.01 | 5.08 ± 0.41 |
| 4. NFD saturated in coconut oil | 0.18 ± 0.05 | 8.01 ± 2.20 |
| 5. NFD saturated in soybean oil | 0.17 ± 0.05 | 8.24 ± 2.05 |
| 6. NFD saturated in jojoba oil | 0.13 ± 0.05 | 6.07 ± 2.08 |
| 7. NFD saturated in babassu oil | 0.14 ± 0.02 | 6.25 ± 0.96 |
| 8. NFD saturated in cottonseed oil | 0.14 ± 0.01 | 6.17 ± 0.48 |
| 9. NFD saturated in Clark A oil | 0.53 ± 0.12 | 23.59 ± 5.62 |
| 10. NFD saturated in mineral oil | 0.01 ± 0.00 | 5.04 ± 0.78 |

As may be seen in the table, the mixed vegetable oil formulation provided significant enhancement relative to the other compositions.

EXAMPLE 5

The above method was then used to compare the penetration of tamoxifen through the skin using a number of different permeation enhancer formulations. Results are set forth in Table 10.

TABLE 10

Tamoxifen Skin Flux Study

| # | Name of Formulation | Av Flux (μg/cm²/hr) |
| --- | --- | --- |
| 1) | Tamoxifen (saturated) in mineral oil | 0.187 ± 0.036 |
| 2) | Tamoxifen (saturated) + 10% mixed vegetable oil in mineral oil | 0.060 ± 0.008 |
| 3) | Tamoxifen (saturated) + 10% olive oil in mineral oil | 0.181 ± 0.055 |
| 4) | Tamoxifen (saturated) + 10% almond oil in mineral oil | 0.133 ± 0.050 |
| 5) | Tamoxifen (saturated) + 10% soybean oil in mineral oil | 0.337 ± 0.054 |
| 6) | Tamoxifen (saturated) + 10% coconut oil in mineral oil | 0.153 ± 0.047 |
| 7) | Tamoxifen (saturated) + 10% cotton seed oil in mineral oil | 0.242 ± 0.02 |
| 8) | Tamoxifen (saturated) + 10% jojoba oil in mineral oil | 0.766 ± 0.08 |
| 9) | Tamoxifen (saturated) + 10% babassu oil in mineral oil | 0.484 ± 0.40 |

Note:
All formulations contain tamoxifen saturated in PG solution.

We claim:

1. A method for enhancing the flux of a drug through the skin, comprising:
applying to the skin of a human patient a composition comprising a pharmaceutically active drug in combination with a permeation enhancing amount of a mixture of vegetable oils selected from the group consisting of almond oil, babassu oil, caster oil, Clark A oil, coconut oil, corn oil, cotton seed oil, jojoba oil, linseed oil, mustard oil, olive oil, palm oil, peanut oil, safflower oil, sesame oil, soybean oil, sunflower-seed oil and wheat germ oil, wherein the drug is present in the composition in an amount in the range of from about 1% to about 10% by weight and the mixture of vegetable oils is present in the composition in an amount in the range of from about 5% to about 25% by weight.

2. The method of claim 1, wherein the mixture of vegetable oils is comprised of a mixture of coconut oil and soybean oil.

3. The method of claim 2, wherein the mixture of vegetable oils is present in an amount in the range of from about 5% to about 10% by weight.

4. The method of claim 2, wherein the mixture of vegetable oils comprises 10% to 90% by weight coconut oil and 90% to 10% by weight of soybean oil.

5. The method of claim 1, wherein the drug is administered in combination with an additional permeation enhancer selected from the group consisting of dimethylsulfoxide, dimethylformamide, N,N-dimethylacetamide, declymethylsulfoxide, polyethylene glycol monolaurate, glycerol monolaurate, lecithin, 1-n-dodecylcyclazacycloheptan-2-one, an alcohol, diethylene glycol monoethylether, and diethylene glycol monomethylether.

6. The method of claim 1, wherein the drug is a narcotic analgesic.

7. The method of claim 6, wherein the drug is buprenorphine or a salt thereof.

8. The method of claim 7, wherein the drug is buprenorphine hydrochloride.

9. The method of claim 1, wherein the drug is a calcium channel blocker or an anti-anginal drug.

10. The method of claim 9, wherein the drug is nifedipine.

11. The method of claim 1, wherein the drug is a sedative.

12. The method of claim 11, wherein the drug is triazolam.

13. The method of claim 1, wherein the drug is an antianxiety drug.

14. The method of claim 13, wherein the drug is alprazolam.

15. The method of claim 1, wherein the drug is an antineoplastic agent.

16. The method of claim 15, wherein the drug is tamoxifen.

17. A composition comprising:
(a) a therapeutically effective amount of a pharmaceutically active drug; and
(b) a permeation enhancing amount of a mixture of vegetable oils selected from the group consisting of almond oil, babassu oil, castor oil, Clark A oil, coconut oil, corn oil, cotton seed oil, jojoba oil, linseed oil, mustard oil, olive oil, palm oil, peanut oil, safflower oil, sesame oil, soybean oil, sunflower-seed oil and wheat germ oil, wherein the drug is present in the composition in any amount in the range of from about 1% to about 10% by weight and the mixture of vegetable oils is present in an amount of about 5% to about 25% by weight.

18. The composition of claim 17, wherein the mixture of vegetable oils is comprised of a mixture of coconut oil and soybean oil.

19. The composition of claim 17, wherein the vegetable oils is present in an amount in the range of from about 5% to about 10% by weight.

20. The composition of claim 18, wherein the mixture of vegetable oils comprises 10% to 90% by weight coconut oil and 90% to 10% by weight of soybean oil.

21. The composition of claim 17, further including an additional permeation enhancer selected from the group consisting of dimethylsulfoxide, dimethylformamide, N,N-dimethylacetamide, declymethylsulfoxide, polyethylene glycol monolaurate, glycerol monolaurate, lecithin, 1-n-dodecylcyclazacycloheptan-2-one, an alcohol, diethylene glycol monoethylether, and diethylene glycol monomethylether.

22. The composition of claim 17, wherein the drug is a narcotic analgesic.

23. The composition of claim 22, wherein the drug is buprenorphine or a salt thereof.

24. The composition of claim 23, wherein the drug is buprenorphine hydrochloride.

25. The composition of claim 17, wherein the drug is a calcium channel blocker or an anti-anginal drug.

26. The composition of claim 25, wherein the drug is nifedipine.

27. The composition of claim 17, wherein the drug is a sedative.

28. The composition of claim 27, wherein the drug is triazolam.

29. The composition of claim 17, wherein the drug is an antianxiety drug.

30. The composition of claim 17, wherein the drug is alprazolam.

31. The composition of claim 17, wherein the drug is an antineoplastic agent.

32. The composition of claim 17, wherein the drug is tamoxifen.

33. A system for the transdermal administration of a drug, comprising:
(a) a matrix reservoir comprised of a polymeric material having dispersed therein a pharmaceutically active drug in a therapeutically effective amount and a permeation enhancing amount of a mixture of vegetable oils selected from the group consisting of almond oil, babassu oil, castor oil, Clark A oil, coconut oil, corn oil, cotton seed oil, jojoba oil, linseed oil, mustard oil, olive oil, palm oil, peanut oil, safflower oil, sesame oil, soybean oil, sunflower-seed oil and wheat germ oil, wherein the drug is present in the matrix in an amount in the range of about 1% to about 10% by weight and the mixture of vegetable oils is present in the composition in an amount in the range of from about 5% to about 25% by weight;

(b) a backing layer positioned on a surface of the matrix; and
(c) a pressure sensitive adhesive layer positioned on a surface of the matrix opposite the surface having the backing layer thereon.

34. The system of claim 33, wherein the mixture of vegetable oils is comprised of a mixture of coconut oil and soybean oil.

35. The system of claim 34, wherein the mixture of vegetables oils is present in an amount in the range of from about 5% to about 10% by weight.

36. The method of claim 34 wherein the mixture of vegetable oils comprises 10% to 90% by weight coconut oil and 90% to 10% by weight of soybean oil.

37. The system of claim 33, further comprising:
an additional permeation enhancer selected from the group consisting of dimethylsulfoxide, dimethylformamide, N,N-dimethylacetamide, declymethylsulfoxide, polyethylene glycol monolaurate, glycerol monolaurate, lecithin, 1-n-dodecylcyclazacycloheptan-2-one, an alcohol, diethylene glycol monoethylether, and diethylene glycol monomethylether.

38. The system of claim 33, wherein the drug is a narcotic analgesic.

39. The system of claim 33, wherein the drug is buprenorphine or a salt thereof.

40. The system of claim 39, wherein the drug is buprenorphine hydrochloride.

41. The system of claim 33, wherein the drug is a calcium channel blocker or an anti-anginal drug.

42. The system of claim 41, wherein the drug is nifedipine.

43. The system of claim 33, wherein the drug is a sedative.

44. The system of claim 43, wherein the drug is triazolam.

45. The system of claim 33, wherein the drug is an antianxiety drug.

46. The system of claim 45, wherein the drug is alprazolam.

47. The system of claim 33, wherein the drug is an antineoplastic agent.

48. The system of claim 47, wherein the drug is tamoxifen.

* * * * *